United States Patent [19]
Brunelli et al.

[11] Patent Number: 5,510,555
[45] Date of Patent: Apr. 23, 1996

[54] CATALYST AND PROCESS FOR OLIGOMERIZING OLEFINS

[75] Inventors: Maurizio Brunelli, San Donato Milanese; Walter Castelvetro, San Giuliano Milanese; Giuseppe Bellussi, Piacenza; Stefano Peratello, Nova Milanese, all of Italy

[73] Assignee: Eniricerche, S.p.A., Milan, Italy

[21] Appl. No.: 193,168

[22] PCT Filed: Oct. 2, 1992

[86] PCT No.: PCT/EP92/02286

§ 371 Date: Feb. 10, 1994

§ 102(e) Date: Feb. 10, 1994

[87] PCT Pub. No.: WO93/06926

PCT Pub. Date: Apr. 15, 1993

[30] Foreign Application Priority Data

Oct. 4, 1991 [IT] Italy ................... MI91A2651

[51] Int. Cl.$^6$ ............... C07C 2/02; C07C 2/04; B01J 21/08; B01J 21/12

[52] U.S. Cl. ............ 585/508; 585/510; 585/520; 502/232; 502/233; 502/237; 502/238; 502/240; 502/245; 502/258; 502/259

[58] Field of Search ............. 502/232, 233, 502/237, 238, 240, 245, 258, 259; 585/508, 510, 520

[56] References Cited

U.S. PATENT DOCUMENTS

| | | | |
|---|---|---|---|
| 4,272,409 | 6/1981 | Bergna | 502/240 |
| 4,414,137 | 11/1983 | Young et al. | 502/233 |
| 4,472,531 | 9/1984 | Speca et al. | 502/237 |
| 4,717,708 | 1/1988 | Cheng et al. | 502/233 |
| 5,169,824 | 12/1992 | Saleh et al. | 502/259 |
| 5,324,878 | 6/1994 | Brunelli et al. | 585/510 |

Primary Examiner—E. Rollins Cross
Assistant Examiner—E. D. Irzinski
Attorney, Agent, or Firm—Rogers & Wells

[57] ABSTRACT

A catalyst, which is active in the oligomerization of olefins is an X-ray-amorphous silica-alumina-nickel oxide gel having an $SiO_2/Al_2O_3$ molar ratio of from 30/1 to 500/1, and $NiO/SiO_2$ molar ratio of from 0.001/1 to 0.01/1, a superficial area of from 500 m$^2$/g to 1.000 m$^2$/g, and a porosity of from 0.3 ml/g to 0.6 ml/g, the means pore diameter being 1 nm (10 Angstrom), and devoid of pores having a diameter over 3 nm (30 Angstrom). The catalyst selectively dimerizes isobutene into alpha- and beta-isobutene and oligomerizes propylene into its relative dimers and trimers. A process is described for preparing the silica-alumina-nickel oxide gel.

23 Claims, No Drawings

CATALYST AND PROCESS FOR OLIGOMERIZING OLEFINS

The present invention relates to a catalytically active silica-alumina-nickel oxide gel, the process for its preparation and its use in processes of dimerization of isobutene into alpha- and beta-diisobutene and oligomerization of propylene into its relative dimers and trimers.

The conventional processes as used in the dimerization of isobutene are generally based on the use of an acidic catalyst, such as sulphuric acid, polyphosphoric acid (in liquid form or supported by an inorganic solid); heteropolyacids i.e. phosphomolybdic and silicotungstic acid; ion exchange resins of the polystyrenesulphonic or fluorosulphonic type; boron trifluoride complexed with alcohols; organic acids, esters, ethers, ketones; aluminium trichloride associated to ethyl ether; hydrochloric acid or nitromethane; simple or complex salts, especially nickel salts activated with an aluminium alkyl, or an aluminium alkyl halide; and metal oxides, as bismuth oxide optionally associated with a phosphor oxide.

Catalysts capable of oligomerizing olefins such as polypropylene and butenes are, again, aluminosilicates and zeolites optionally modified with salts or oxides of metals such as nickel, chromium and cobalt, as for instance described in U.S. Pat. No. 3,518,323 and U.S. Pat. No. 3,525,456, in EP-A-132 172, EP-A-224 220, EP-A-133 052.

Finally, in U.S. Pat. No. 3,960,978, U.S. Pat. No. 4,150,062, as well as in EP-A-311.675 processes are described for the production of gasoline by means of olefin oligomerization with ZMS-5 type zeolites.

The gasolines so obtained also contain a fraction of aromatic hydrocarbons, mainly benzene, that which is undesirable due to its toxicity towards human beings and the environment.

Many of the conventional oligomerization catalysts have drawbacks due to the corrosive action of the acids that are used, to the requirement of disposing of the exhausted catalysts, their limited life and/or the cost of their preparation. A problem which is common to these conventional catalysts lies in their poor selectivity to the desired reaction products. For instance, when used in the dimerization of isobutene, they cause the formation of relevant amounts of higher oligomers and isomers other than the most appreciable ones, that is, alpha- and beta-diisobutene.

Finally whenever an isobutene stream admixed with other C4 olefins undergoes dimerization, codimers are usually and concurrently produced.

This is believed to be due to the comparatively high temperatures are which the conventional catalysts unfold their activity, or the exceedingly high acidity of the catalysts themselves, which encourage molecular rearrangements or other undesirable side-reactions.

EP-A-340.868 discloses an amorphous and microporous silica-alumina gel which is active in processes of isomerization, alkylation, dewaxing and dimerization of linear olefins.

According to the present invention it has now been ascertained that the introduction of a limited amount of nickel oxide in a gel of the type suggested in the aforementioned EP-A 340 868 makes it possible to obtain a catalyst having an even and controlled porosity, essentially free from any isomerizing capability and capable of dimerizing isobutene into alpa- and beta-diisobutene with a surprisingly high selectivity. It is therefore possible to obtain high quality products, useful as chemical intermediate or in the preparation of high-octane gasoline. It has furthermore been ascertained that such a catalyst is active in the oligomerization of propylene into dimers and trimers, which are useful, as such or after etherification, as high-octane gasolines.

According to the foregoing, a first aspect the present invention relates a silica-alumina-nickel oxide gel, amorphous to X-rays, having an $SiO_2/Al_2O_3$ molar ratio of from 30/1 to 500/1, and $NiO/SiO_2$ molar ratio of from 0,001/1 to 0,05/1, a surface area from 500 $m^2/g$ to 1.000 $m^2/g$, a mean pore diameter of about 1 nm (10 Å) (Angstrom), and a porosity from 0,3 ml/g to 0,6 ml/g, devoid of pores having a diameter over 3 nm (30 Å).

In the preferred embodiment the silica-alumina-nickel oxide gel of this invention has a molar ratio $SiO_2/Al_2O_3$ of 100/1, a molar ratio $NiO/SiO_2$ of 0,02/1, a surface area of 800 $m^2/g$ and a porosity of 0.4–0.5 ml/g.

According to another aspect, the present invention relates to a process for preparing a silica-alumina-nickel oxide gel, having the above mentioned features, which comprises the steps of:

(i) preparing an aqueous solution of a water soluble aluminium compound susceptible of being hydrolyzed to $Al_2O_3$ and of a tetralkylammonium hydroxide, wherein the alkyl is selected from ethyl,n.propyl and n.butyl;

(ii) preparing an aqueous solution of a water soluble nickel carboxylate and a water soluble organic amine;

(iii) mixing the two (i) and (ii) solutions and adding thereto a water soluble silicon compound susceptible of being hydrolyzed to $SiO_2$, to obtain a homogeneous gel, and (iv) drying the gel and calcining it initially in an inert atmosphere and finally in an oxidizing atmosphere.

The aluminium compounds used are preferably aluminium trialkoxides i.e. aluminium tri-n.-propoxide and aluminium tri-isopropoxide.

The nickel carboxylate is preferably a nickel salt of an aliphatic carboxylic acid and especially nickel acetate. Silicon compounds are preferably the tetraalkyl silicates, such as tetraethylsilicate. These reactants shall profitably be employed in such a mutual ratio as to obtain the composition which is desired for the silica-alumina-nickel oxide gel, on bearing in mind that the reaction yield is virtually quantitative.

The organic amine is preferably an aliphatic amine, especially ethylenediamine. Advisably, an amount of the amine is employed which is such as to have a molar ratio of the amine to the nickel carboxylate of about 2/1.

The preparation of the solutions and their admixture are conveniently carried out at room temperature, or at a temperature close to room temperature. The hydrolysis of step (iii) is carried out at a temperature of from 50° C. to 70° C., and preferably of 60° C. Under such conditions, the time required for complete gelling varies from 15 min to 5 hours, as a function of the preselected temperature, and in the preferred embodiment it is of from 25 min to 60 min.

The drying step (iv) is conveniently carried out at a temperature below 150° C. and preferably of from 90° C. to 100° C., for a time sufficient to remove water completely. The calcination of step (iv) is carried out in an atmosphere which is initially inert (such as nitrogen) and then oxidizing (such as air) at a temperature of from 500° C. to 700° C., preferred being of from 550° C. to 600° C., for times of from 4 hours to 20 hours, as a function of the preselected temperature, and which, in the preferred embodiment are of from 6 hours to 16 hours.

The silica-alumina-nickel oxide gel thus obtained can be granulated into particles of the desired size, or can be supported by an appropriate inert solid substrate material, or it can also be admixed with an inert solid material. More particularly, the gel can be admixed with appropriate metal oxides, which essentially act as binders.

Oxides which are suitable to this purpose are aluminas, silicas and the oxides of titanium, magnesium and zirconium. The gel and the binder can be blended in weight ratios of from 50:50 to 95:5, preferred being from 30:90 to 90:10. The two components can be blended with the conventional means and the blend is conveniently compacted in the desired final shape, such as in the forms of extrudates and granulates. By so doing, it is possible to impart improved mechanical properties to the catalyst.

According to a further embodiment, the present invention relates to an olefin oligomerization process which uses as the catalyst the silica-alumina-nickel oxide gel referred to above.

By oligomerization, to the ends of the present disclosure, the conversion of isobutene is intended into mixtures which essentially consist of alpha- and beta-dimers of diisobutene and by oligomerization the conversion of propylene into mixtures which are essentially comprised of propylene dimers and trimers.

The oligomerization reaction can be carried out as a continuous or a semicontinuous process or as a batch-process, by working in liquid, gaseous or mixed form (liquid-vapour). When working discontinuously, the conveniently employed catalyst amount is from 1% to 50% relative to the olefin, at a temperature of from 50° C. to 150° C., preferred being from 55° C. to 80° C., under a pressure of from 1 ata to 200 ata, preferred being from 1 ata to 6 ata.

For the semicontinuous or continuous runs, it is convenient to work at a temperature of from 50° C. to 200° C., preferred being from 50° C. to 150° C., at a spatial velocity (WHSV) for the olefin of from 0,5 $h^{-1}$ to 8 $h^{-1}$. At any rate, it is possible to use pure olefins or olefins admixed with other olefins and/or paraffins. The oligomerization reaction is exothermic, so that the reactor temperature should be checked to prevent that an exceedingly high rise may be conducive to the formation of higher oligomers and/or undesirable isomerization phenomena.

As outlined above, the olefins to be oligomerized according to the process of this invention are isobutene and propylene. More particularly, the oligomerization of isobutene selectively proceeds towards the formation of the two isomers of the 2,4,4-trimethyl-1-pentene (alpha-diisobutene) and 2,4,4-trimethyl-2-pentene (beta-diisobutene) dimer.

These dimers can be used as chemical intermediates for preparing non-ionic surfactants, cross-linking agents for elastomers, plasticizers, and other chemicals, by alkylation, amination or carbonylation reactions.

In addition, the alpha- and the beta-diisobutene are useful when preparing high-octane gasolines since they exhibit RON and MON values (leadless): RON=106 and MON=86,5 (alpha isomer) and RON=103,5 and MON=86,2 (beta isomer) and can be hydrogenated to isooctane (2,2,4-trimethylpentane) having RON=100 and MON=100.

When oligomerizing propylene, one predominantly obtains an oligomer mixture which prevailingly contains a high-octane gasoline fraction (boiling point from $C_5$ at 175° C.) together with a small amount of a hydrocarbon fraction having a higher molecular weight (boiling point from 175° to 370° C.).

The ensuing experimental examples are reported to better illustrate.

EXAMPLE 1

Preparation of the Catalyst (A) Solution 2 g of aluminium isopropylate are dissolved, at room temperature, in 68,5 g of a 13,35% by weight-aqueous solution of tetrapropylammonium hydroxide (TPA—OH).

(B) Solution 1,85 g of nickel acetate are dissolved in 75,6 of demineralized water and 1,25 g of ethylenediamine (EDA) are added thereto.

The solutions (A) and (B) are combined, and the mixture is heated to 60° C.: to the heated mixture there are added 104,1 g of tetraethylsilicate (TES).

The resultant mixture has the following molar ratios:

$SiO_2/Al_2O_3$=102

TPA—$OH/SiO_2$=0,09

$NiO/SiO_2$=0,021

EDA/NiO=2

This mixture is kept stirred at 60° C. for 40 min, until obtaining a homogeneous gel, which is dried in an air stream at 90° C. and then calcined at 550° C., first in a nitrogen stream for 3 hours, and then in an air stream for 10 hours.

A silica-alumina-nickel oxide gel is obtained, with a quantitative yield relative to the initially charged materials, said gel being granulated into 1 mm–2 mm particles.

The catalyst so prepared has the following specifications:

X-ray amorphous (powder analysis by a Philips vertical goniometer, using the CuKa radiation;

$SiO_2/Al_2O_3$ molar ratio=102;

$NiO/SiO_2$ molar ratio=0,021;

Surface area=800 $m^2$/g (measured with the B.E.T. method in a Carlo Erba Sorptomatic 1880 apparatus);

Porosity=0,44 ml/g (mean pore diameter 1 nm (10 Angstrom), and absence of pores having a diameter over 3 nm (30 Angstrom): (values determined by the Carlo Erba Sorptomatic 1880 apparatus).

EXAMPLE 2

A glass vial, which has been flame-sealed in a nitrogen atmosphere and containing 2,13 g of the catalyst prepared according to Example 1 and the finely ground in a mortar and heated to 550° C. for 6 hours, is introduced into a 200-ml autoclave. The autoclave is evacuated, charged at a nitrogen pressure of 1,01325 bar (1 ata) and 9,4 g of isobutene are condensed in the cold therein.

The reaction, of isobutene dimerization is started by rupturing the catalyst-containing vial by the mechanical stirrer with which the autoclave is equipped.

Dimerization is a strongly exothermic reaction and the actual reaction temperature is monitored by a thermocouple inserted into the autoclave interior.

By varying the temperature of the bath, is is possible to check the temperature oscillations within ±2° C. During the entire reaction run, the pressure within the autoclave is essentially due to the vapour pressure of the unreacted isobutene. Consequently, while the initial pressure was about 6,195 bar (6 ata), corresponding to the vapour pressure of the isobutene in equilibrium with its liquid phase, as dimerization proceeds, the pressure decreases due to the disappearance of the isobutene liquid phase, followed by the gradual disappearance of the relevant vapour phase.

The reaction mixture is sampled at different times from the autoclave, by a dip tube, and the samples are condensed in test tubes fitted with an appendix for the subsequent analyses. During the entire reaction run a vigorous mechanical stirring is maintained to ensure both a satisfactory contact between the liquid and the solid (catalyst) phases, and a good homogeneousness of the mixture during sampling.

The values of the conversion and the quantitative analysis of the mixed products corresponding to the several samplings is effected gaschromatographically, with a wide-bore-column Hewlett Packard chromatographer, containing an apolar stationary phase RSL300, at a temperature which is programmed for 30° C. to 280° C.

The quantitative determination of the several isomers of the isobutene dimer, that is, 2,4,4-trimethyl-1-pentene (alpha diisobutene) and 2,4,4-trimethyl-2-pentene (beta diisobutene) is carried out gaschromatographically again, by using a capillary column with stationary apolar phase SP81 which permits the separation of the isomers, whereas their structural identification is carried out on a mixture which contains 96% of the dimer, and is obtained by fractional distillation of the first fraction sampled during the reaction, by means of a mass spectrometer matched to a capillary-column gaschromatographer, on the basis of the $^1H$ and $^{13}C$ NMR.

The results are tabulated on Table 1.

EXAMPLE 3

The procedure is similar to that of Example 2, with the same catalyst as in Example 2, which has been reactivated by heating to 550° C. for 6 hours, the reaction temperature being the same as in Example 2, but with a catalyst weight percentage halved relative to that of Example 2.

More particularly, the autoclave is charged with 2 g of activated catalyst and 18 g of isobutene.

In this case, the starting temperature is 55° C., so that the thermal-contribution afforded by the dimerization reaction brings about a rise to 60° C. of the internal temperature of the autoclave (temperature of the oil bath) during the first 60 s, whereafter the reaction temperature is fairly stabilized.

The results of this example are tabulated on Table 1.

TABLE 1

|  | EX. 2 | EX. 3 |
| --- | --- | --- |
| Temperature, °C. | 60 | 60 |
| Catalyst, % wt. | 22 | 11 |
| Isobutene Conversion, % | | |
| after 2 min | 15 | 15 |
| after 6 min | 20 | 28 |
| after 15 min | 75 | 40 |
| after 60 min | — | 99 |
| Oligomer Composition, % | | |
| C8: | | |
| after 2 min | 85 | 75 |
| after 6 min | 86 | 83 |
| after 15 min | 72 | 78 |
| after 60 min | — | 50 |
| C12: | | |

TABLE 1-continued

|  | EX. 2 | EX. 3 |
| --- | --- | --- |
| after 2 min | 10 | 20 |
| after 6 min | 11 | 14 |
| after 15 min | 23 | 19 |
| after 60 min | — | 43 |
| C16 and higher: | | |
| after 2 min | 5 | 5 |
| after 6 min | 3 | 3 |
| after 15 min | 5 | 5 |
| after 60 min | — | 5 |
| Dimer Composition: | | |
| alpha | | |
| after 2 min | 90 | 89 |
| after 6 min | 84 | — |
| after 15 min | 83 | 86 |
| beta | | |
| after 2 min | 10 | 11 |
| after 6 min | 14 | — |
| after 15 min | 15 | 14 |
| Others: | | |
| after 2 min | traces | traces |
| after 6 min | 2 | — |
| after 15 min | 2 | traces |

EXAMPLE 4

A steel flux-reactor having an inside diameter of 12 mm, heated by an electric oven, is charged with 3,0 g (5 ml) of the catalyst prepared according to Example 1. The reactor is fed with propylene under the following working conditions:

| Inlet temperature | 80° C. |
| --- | --- |
| Hot spot temperature | 94° C. |
| Pressure | 30,8 bar (30 ata) |
| Spatial velocity | 2,87 h$^{-1}$ |

Under the conditions reported above, the following results are obtained:

| Propylene conversion | 79% |
| --- | --- |
| Hexenes | 45% |
| Nonenes | 40% |
| Oligomers higher than C9 | 15% |

The fraction of the product which contains hydrocarbons having up to 9 carbon atoms is a high-grade gasoline exhibiting values of ROM=97 and MON=84 (leadless).

EXAMPLE 5

To the flux-reactor of Example 4, charged with the same catalyst and the same amounts of reactants, propylene is fed under the following working conditions:

| Inlet temperature | 120° C. |
| --- | --- |
| Hot spot temperature | 135° C. |
| Pressure | 30,8 bar (30 ata) |
| Spatial velocity | 4,59 h$^{-1}$ |

Under the conditions reported above, the following results are obtained:

| | |
|---|---|
| Propylene conversion | 73% |
| Hexenes | 25% |
| Nonenes | 35% |
| Oligomers higher than C9 | 40% |

The fraction of the product which contains hydrocarbons having up to 9 carbon atoms is a high-grade gasoline exhibiting values of ROM=97 and MON=84 (leadless).

We claim:

1. An X-ray-amorphous silica-alumina-nickel oxide gel having: (a) an $SiO_2/Al_2O_3$ molar ratio of from 30/1 to 500/1; (b) an $NiO/SiO_2$ molar ratio of from 0.001/1 to 0.05/1; (c) a surface area of from 500 $m^2/g$ to 1000 $m^2/g$; and (d) a porosity of from 0.3 ml/g to 0.6 ml/g, the mean pore diameter being 1 nm, and devoid of pores having a diameter over 3 nm, said gel having catalytic activity.

2. The gel of claim 1, wherein the $SiO_2/Al_2O_3$ molar ratio is 100/1, the $NiO/SiO_2$ molar ratio is 0.02/1, the surface area is 800 $m^2/g$ and the porosity is from 0.4 to 0.5 ml/g.

3. The gel of claim 1 or 2, wherein said gel is supported by an inert solid substrate.

4. The gel of claim 1 or 2, wherein said gel is admixed with an inert solid material.

5. The process for preparing the gel of claim 1 or claim 2, comprising the steps of: (i) preparing an aqueous solution of a water-soluble aluminum compound susceptible of being hydrolyzed to $Al_2O_3$ and of a tetraalkylammonium hydroxide, wherein the alkyl is selected from ethyl, n-propyl, and n-butyl; (ii) preparing an aqueous solution of a water-soluble nickel carboxylate and a water-soluble organic amine; (iii) mixing solutions (i) and (ii) and adding thereto a water-soluble silicon compound susceptible of being hydrolyzed to $SiO_2$, to obtain a homogenous gel; and (iv) drying the gel and calcining it first in an inert atmosphere and finally in an oxidizing atmosphere.

6. The process of claim 5, wherein in step (i) the aluminum compounds are aluminum trialkoxides.

7. The process of claim 6, wherein the aluminum trialkoxides are aluminum tri-n-propoxide and aluminum tri-isopropoxide.

8. The process of claim 5, wherein in step (ii) the nickel carboxylates are nickel salts of an aliphatic carboxylic acid, and the organic amines are aliphatic diamines, with a molar ratio of the amine to the nickel carboxylate of 2:1.

9. The process of claim 8, wherein the nickel salt of an aliphatic carboxylic acid is nickel acetate, and the aliphatic diamine is ethyleneamine.

10. The process of claim 5, wherein in step (ii) the silicon compounds are tetraalkyl silicates.

11. The process of claim 10, wherein the tetraalkyl silicate is tetraethylsilicate.

12. The process of claim 5, wherein the hydrolysis of step (iii) is carried out at a temperature of from 50° C. to 70° C., and for a time of from 15 minutes to 5 hours.

13. The process of claim 12, wherein the hydrolysis of step (iii) is carried out at a temperature of 60° C., and for a time of from 25 minutes to 60 minutes.

14. The process of claim 5, wherein the drying step (iv) is carried out at a temperature below 150° C. for a time sufficient to remove water completely, the calcination being carried out in an atmosphere which is initially inert, and then in an oxidizing atmosphere, at a temperature of from 500° C. to 700° C., for a time of from 4 hours to 20 hours.

15. The process of claim 14, wherein the drying step (iv) is carried out at a temperature of from 90° C. to 100° C., the calcination being carried out in nitrogen, and then in air, at a temperature of from 550° C. to 600° C., for a time of from 6 hours to 16 hours.

16. A process for dimerizing isobutene into alpha- and beta-isobutene, comprising the step of contacting isobutene in dimerization conditions with the gel of claim 1.

17. A process for preparing propylene dimers and trimers, comprising the step of contacting propylene, under oligomerization conditions, with the gel of claim 1.

18. The process of claim 16 or 17, wherein the process is carried out as a batch process, with an amount of catalyst of from 1% by weight to 50% by weight relative to the olefin, at a temperature of from 50° C. to 150° C., under a pressure of from 1 atm to 200 atm.

19. The process of claim 18, wherein the process is carried out at a temperature of from 55° C. to 80° C., under a pressure of from 1 atm to 6 atm.

20. The process of claim 16 or 17, wherein the process is carried out as a semicontinuous process, at a temperature of from 50° C. to 200° C., at a spatial velocity of the olefin (WHSV) of from 0.5 $h^{-1}$ to 8 $h^{-1}$.

21. The process of claim 20, wherein the process is carried out at a temperature of from 50° C. to 150° C.

22. The process of claim 16 or 17, wherein the process is carried out as a continuous process, at a temperature of from 50° C. to 200° C., at a spatial velocity of the olefin (WHSV) of from 0.5 $h^{-1}$ to 8 $h^{-1}$.

23. The process of claim 22, wherein the process is carried out at a temperature of from 50° C. to 150° C.

\* \* \* \* \*